(12) United States Patent
Claffey et al.

(10) Patent No.: US 8,883,812 B2
(45) Date of Patent: Nov. 11, 2014

(54) PIPERIDINYL PYRIMIDINE AMIDES AS KV7 POTASSIUM CHANNEL OPENERS

(75) Inventors: Michelle Marie Claffey, Stonington, CT (US); Jennifer Elizabeth Davoren, Cambridge, MA (US); John Adams Lowe, III, Stonington, CT (US); Robert Joseph Mather, Hope Valley, RI (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/808,355

(22) PCT Filed: Jun. 20, 2011

(86) PCT No.: PCT/IB2011/052686
§ 371 (c)(1), (2), (4) Date: Jan. 4, 2013

(87) PCT Pub. No.: WO2012/004698
PCT Pub. Date: Jan. 12, 2012

(65) Prior Publication Data
US 2013/0150391 A1    Jun. 13, 2013

Related U.S. Application Data

(60) Provisional application No. 61/362,505, filed on Jul. 8, 2010.

(51) Int. Cl.
C07D 401/04 (2006.01)
A61K 31/4523 (2006.01)
A61K 31/506 (2006.01)
A61K 45/06 (2006.01)

(52) U.S. Cl.
CPC ........... *A61K 31/506* (2013.01); *A61K 31/4523* (2013.01); *A61K 45/06* (2013.01); *C07D 401/04* (2013.01)
USPC .......................................... 514/273; 544/320

(58) Field of Classification Search
CPC .......................... C07D 401/04; A61K 31/4523
USPC .......................................... 544/320; 514/273
See application file for complete search history.

(56) References Cited

U.S. PATENT DOCUMENTS

| | | | |
|---|---|---|---|
| 2006/0167248 | A1 | 7/2006 | Tornoe et al. |
| 2007/0066612 | A1 | 3/2007 | Khanzhin et al. |
| 2008/0139610 | A1 | 6/2008 | Vernier et al. |
| 2008/0261918 | A1 | 10/2008 | Showell et al. |
| 2008/0318979 | A1 | 12/2008 | Vernier et al. |
| 2009/0118285 | A1 | 5/2009 | Husum Bak-Jensen et al. |
| 2010/0256145 | A1 | 10/2010 | Bak-Jensen et al. |

FOREIGN PATENT DOCUMENTS

| | | |
|---|---|---|
| WO | 2005087754 | 9/2005 |
| WO | 2006064277 | 6/2006 |
| WO | 2007090409 | 8/2007 |
| WO | 2008024398 | 2/2008 |
| WO | 2009015667 | 2/2009 |

OTHER PUBLICATIONS

Yi et al., Colloqium: Controlling potassium channel activities: Interplay between the membrane and intracellular factors, PNAS, vol. 98, No. 20, Sep. 25, 2001.*
Cooper, E.C, et al., M-Channels, Neurological Diseases, Neuromodulation, and Drug Development, Archives of Neurology, Apr. 2003, pp. 496-500, 60(4).
Azar, N.J., et al., "Considerations in the Choice of an Antiepileptic Drug in the Treatment of Epilepsy", Seminars in Neurology, Jul. 2008, pp. 305-315, 28(3).
Wickendon, A.D., et al., "Retigabine, A Novel Anti-Convulsant, Enhances Activation of KCNQ2/Q3 Potassium Channels", Molecular Pharmacology, Sep. 1, 2000, pp. 591-600, 58(3).
Henshall, David C., et al., "Electroencephalographic and Behavioral Convulsant Effects of Hydrobromide and Hydrochloride Salts of Bupropion in Conscious Rodents", Neuropsychiatric Disease and Treatment, 2009, pp. 189-206, vol. 5.
Shackelford, S.A., et al., "Electrophilic Tetraalkylammonium Nitrate Nitration. II. Improved Anhydrous Aromatic and Heteroaromatic Mononitration with Tetramethylammonium Nitrate and Triflic Anhydride, Including Selected Microwave Examples", Journal of Organic Chemistry, Jan. 24, 2003, pp. 267-275, 68(2).
PCT/IB2011/052686, International Search Report dated Aug. 31, 2011, 5 pages.

* cited by examiner

*Primary Examiner* — Deepak Rao
(74) *Attorney, Agent, or Firm* — Richard V. Zanzalari

(57) ABSTRACT

The present invention relates to compounds of Formula (I) as described herein or a pharmaceutically acceptable salt thereof, pharmaceutical composition comprising a compound of Formula (I) or a pharmaceutically acceptable salt thereof and methods of treating, or manufacture of a medicament to treat, a disease, disorder, or condition of the central nervous system, including bipolar disorder, depressive disorders, anxiety disorders, cognitive disorders, pain disorders, urogentital disorder, and epilepsy, among the other diseases, disorders or conditions discussed herein as mono-therapy or in combination with another active pharmaceutical ingredient.

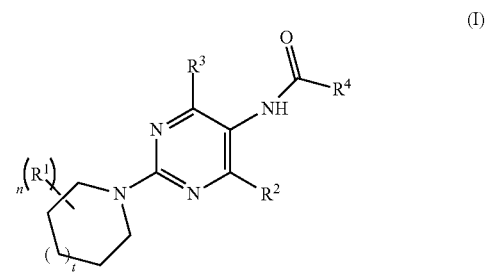

4 Claims, No Drawings

PIPERIDINYL PYRIMIDINE AMIDES AS KV7 POTASSIUM CHANNEL OPENERS

This application is a national stage application under 35 U.S.C. 371 of PCT/IB2011/052686, filed on Jun. 20, 2011, which claims the benefit of U.S. Patent Application No. 61/362,505, filed on Jul. 8, 2010, the disclosures of which are hereby incorporated by reference in their entirety.

FIELD OF THE INVENTION

The present invention relates to dimethoxy-pyrimidine amides and to pharmaceutical compositions containing them and to their use in the treatment of central nervous system disorders, including bipolar disorder, depressive disorders, anxiety disorders, cognitive disorders, pain disorders, urogentital disorder, epilepsy and other disorders in mammals, including humans. The present invention relates to compounds, which are openers of voltage dependent potassium channels of the Kv7.2/7.3 or KCNQ2/3 subtype. The compounds are useful in the treatment of disorders and diseases affected by dampening the excitability of tissues expressing and responsive to the Kv7 family (Kv7.2, 7.3, 7.4, 7.5 subtypes) of voltage dependent potassium channels. These compounds have been shown to facilitate the opening of the Kv7.2-5 voltage dependent potassium channels

BACKGROUND OF THE INVENTION

Kv7.2/3 channels are voltage-gated potassium channels that modulate neuronal excitability in the central and peripheral nervous systems. Blockade of Kv7.2./7.3.channels, for example, by acetylcholine, increases neuronal excitability, whereas channel opening decreases it. Kv7 channels are expressed as homo or heterotetramers, composed of different subunit combinations. A deficiency in these channels is the underlying cause of a rare form of neonatal epilepsy, and polymorphisms in the Kv7.3 gene are associated with bipolar disorder based on linkage studies. The known Kv7 openers flupirtine (2-amino-6-[[(4-fluorophenyl)methyl]amino]-3-pyridinyl]-carbamic acid ethyl ester) and retigabine (N-(2-amino-4-(4-fluorobenzylamino)-phenyl)carbamic acid ethyl ester)) have shown numerous clinical applications, including, inter alia, epilepsy, pain, and cognitive function.

United States Patent Application 2007/0066612 relates to substituted pyrimidine derivatives which are alleged to be openers of the KCNQ family potassium ion channels, and, therefore, useful in the treatment of disorders and diseases being responsive to opening of the KCNQ family potassium ion channels, one such disease is epilepsy.

The present invention relates to dimethoxy-pyrimidine amide compounds of Formula I that exhibit activity as Kv7.2-5 channel openers.

SUMMARY OF THE INVENTION

The present invention relates to compounds of Formula I as described below, or a pharmaceutically acceptable salt thereof, or a stereoisomer of the compound of Formula I or a pharmaceutically acceptable salt thereof.

This invention also relates to a pharmaceutical composition comprising a compound of Formula I, or a pharmaceutically acceptable salt thereof, or a stereoisomer of the compound of Formula I or a pharmaceutically acceptable salt thereof, and at least one pharmaceutically acceptable excipient.

This invention also is directed to a method of treating, or manufacture of a medicament to treat, a disease, disorder or condition of the central nervous system, including bipolar disorder, depressive disorders, anxiety disorders, cognitive disorders, pain disorders, urogentital disorder, and epilepsy, among the other diseases, disorders, or conditions discussed herein as mono-therapy or in combination with one or more pharmaceutical active ingredient.

DETAILED DESCRIPTION OF THE INVENTION

An embodiment of the invention is a compound of Formula I

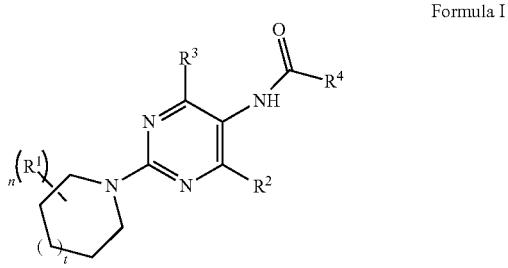

Formula I wherein:
n is an integer of 1 or 2;
t is 0 or 1;
Each $R^1$ is independently selected from $C_{1-3}$ alkoxy, $C_{1-3}$ alkyl, $C_{1-3}$ alkyl-O—$C_{1-3}$ alkyl;
$R^2$ and $R^3$ are independently $C_{1-3}$ alkyl, $C_{1-3}$ alkoxy, or $C_{3-6}$cyloalkyl provided that at least one is $C_{1-3}$ alkoxy;
$R^4$ is $C_{1-6}$ alkyl, $C_{1-3}$ alkyl-$C_{3-6}$cyloalkyl, $C_{3-6}$ heterocycloalkyl;
or a pharmaceutically acceptable salt thereof.

This invention also relates to compounds of Formula I where $R^1$, $R^2$, and $R^3$ are each $C_{1-3}$ alkoxy; $R^4$ is $C_{4-6}$ alkyl, and where n and t are each 1.

This invention also relates to compounds of Formula I where $R^1$, $R^2$, and $R^3$ are each methoxy; $R^4$ is —$CH_2$-t-butyl, and where n and t are each 1.

Also desired are novel compounds with improved properties relative to known compounds, which are openers of the KCNQ family potassium channels, such as retigabine. Improvement of one or more of the following parameters is desired: half-life, clearance, and selectivity, interactions with other medications, bioavailability, potency, formulability, chemical stability, metabolic stability, membrane permeability, solubility and therapeutic index. The improvement of such parameters may lead to improvements such as: an improved dosing regime by reducing the number of required doses a day, ease of administration to patients on multiple medications, reduced side effects, enlarged therapeutic index, improved tolerability or improved compliance.

ABBREVIATIONS AND DEFINITIONS

Unless otherwise indicated, as used herein, the terms "halogen" and "halo" include fluoro, chloro, bromo, and iodo.

Unless otherwise indicated, as used herein, the term "alkyl" includes saturated monovalent hydrocarbon radicals containing from one to six carbon atoms unless otherwise specified and having straight, or branched moieties. Examples of alkyl groups include methyl, ethyl, n-propyl, isopropyl, and t-butyl.

Unless otherwise indicated, as used herein, the term "cycloalkyl" includes saturated monovalent hydrocarbon cyclic moieties. Examples of cycloalkyl groups include cyclopropyl, cyclobutyl, cyclopentyl, and cyclohexyl.

Unless otherwise indicated, as used herein, the term "alkoxy", means "alkyl-O—", wherein "alkyl" is as defined above. Examples of "alkoxy" groups include methoxy, ethoxy, propoxy, butoxy, pentoxy, allyloxy, and O-cycloalkyl.

Unless otherwise indicated, as used herein, the term heterocycloalkyl means a mono-cycloalkyl moiety of 3 to 10 carbons where at least one carbon atom has been replaced with a heterotom selected from nitrogen, oxygen, or sulfur and where not all of the carbon atoms must be part of the ring. Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, methyloxetanyl, tetrahydrodiazinyl, oxazinyl, oxathiazinyl, indolinyl, isoindolinyl, quinuclidinyl, chromanyl, isochromanyl, benzoxazinyl, and the like.

Unless otherwise indicated, the term "one or more" substituents, or "at least one" substituent as used herein, refers to from one to the maximum number of substituents possible based on the number of available bonding sites. Examples of "one or more" or "at least one" substituent include 1 to 3 substituents on a terminal methyl, e.g., 3 available bonding sites where the fourth bonding site is from the methyl to molecule for which carbon of the methyl is a terminal atom.

One of ordinary skill in the art will appreciate how each group discussed herein may attach as $R^1$, $R^2$, $R^3$, or $R^4$ to the compound of Formula I by any atom available for bonding.

The following abbreviations are used herein:
DMF: Dimethylformamide
EtOAc: Ethyl acetate
HPLC: High pressure liquid chromatography
LCMS: Liquid chromatography-mass spectrometry
MeCN: Acetonitrile
MeOH: Methanol
MS: Mass spectrometry
RT: Room temperature
TFA: Trifluoroacetic acid
THF: Tetrahydrofuran Specific embodiments of the present invention are shown in the Examples below.

Compounds of Formula I may have optical centers and therefore may occur in different enantiomeric and diastereomeric configurations. The present invention includes all enantiomers, diastereomers, and other stereoisomers of such compounds of Formula I, as well as racemic compounds and racemic mixtures and other mixtures of stereoisomers thereof.

Compounds of Formula I include all forms of the compound of Formula I, including solvates including hydrates when the solvent, isomers, crystalline and non-crystalline forms, isomorphs, polymorphs, metabolites, and prodrugs thereof. For example, the compounds of Formula I, or a pharmaceutically acceptable salt thereof, may exist in unsolvated and solvated forms. When the solvent, including water, is tightly bound, the complex will have a well-defined stoichiometry independent of humidity. When, however, the solvent is weakly bound, as in channel solvates and hygroscopic compounds, the solvent content will be dependent on humidity and drying conditions. In such cases, non-stoichiometry will be the norm; this routinely occurs when one is a isolating final compound from a reaction mixture, and upon drying, residual solvent, including water, remains present. Failure to provide peaks in reporting spectral data of said solvates, including hyrdates, is normal because one of ordinary skill in the art would expect such solvates to be present and normally reports only peaks used to identify structure and normally does not report solvent peaks. Therefore, when referring to a compound of Formula I or a compound of the invention, it is meant to include residual solvent including water, isomers, crystalline and non-crystalline forms, isomorphs, enantiomers, diastereomers, other stereoisomers polymorphs, metabolites, and prodrugs of the compounds of Formula I and also of the corresponding pharmaceutically acceptable salts thereof.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-Na^+$) or non-ionic (such as —$N^-N^+(CH_3)_3$) polar head group. For more information, see *Crystals and the Polarizing Microscope* by N. H. Hartshorne and A. Stuart, 4th Edition (Edward Arnold, 1970).

The compounds of the invention include compounds of Formula I as hereinbefore defined, including all polymorphs and crystal habits thereof, prodrugs and isomers thereof (including optical, geometric and tautomeric isomers) as hereinafter defined and isotopically-labeled compounds of Formula I.

As indicated, so-called 'prodrugs' of the compounds of Formula I are also within the scope of the invention. Thus, certain derivatives of compounds of Formula I which may have little or no pharmacological activity themselves can, when administered into or onto the body, be converted into compounds of Formula I having the desired activity, for example, by hydrolytic cleavage. Such derivatives are referred to as 'prodrugs'. Further information on the use of prodrugs may be found, for example, in *Pro-drugs as Novel Delivery Systems*, Vol. 14, ACS Symposium Series (T. Higuchi and W. Stella). See also *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in *Design of Prodrugs* by H. Bundgaard (Elsevier, 1985).

Some examples of prodrugs in accordance with the invention include
 (i) where the compound of Formula I contains a carboxylic acid functionality (—COOH), an ester thereof, for example, a compound wherein the hydrogen of the carboxylic acid functionality of the compound of Formula I is replaced by ($C_1$-$C_8$)alkyl;
 (ii) where the compound of Formula I contains an alcohol functionality (—OH), an ether thereof, for example, a compound wherein the hydrogen of the alcohol functionality of the compound of Formula I is replaced by ($C_1$-$C_6$)alkanoyloxymethyl; and
 (iii) where the compound of Formula I contains a primary or secondary amino functionality (—$NH_2$ or —NHR where R is not H), an amide thereof, for example, a compound wherein, as the case may be, one or both hydrogens of the amino functionality of the compound of Formula I is/are replaced by ($C_1$-$C_{10}$)alkanoyl.

Further examples of replacement groups in accordance with the foregoing examples and examples of other prodrug types may be found in the aforementioned references.

Moreover, certain compounds of Formula I may themselves act as prodrugs of other compounds of Formula I.

Also included within the scope of the invention are metabolites of compounds of Formula I, that is, compounds formed in vivo upon administration of the drug. Some examples of metabolites in accordance with the invention include
 (i) where the compound of Formula I contains a methyl group, an hydroxymethyl derivative thereof (—$CH_3$→—$CH_2OH$):
 (ii) where the compound of Formula I contains an alkoxy group, an hydroxy derivative thereof (—OR→—OH);
 (iii) where the compound of Formula I contains a tertiary amino group, a secondary amino derivative thereof (—$NR^1R^2$→—$NHR^1$ or —$NHR^2$);
 (iv) where the compound of Formula I contains a secondary amino group, a primary derivative thereof (—$NHR^1$→—$NH_2$);
 (v) where the compound of Formula I contains a phenyl moiety, a phenol derivative thereof (-Ph→-PhOH); and
 (vi) where the compound of Formula I contains an amide group, a carboxylic acid derivative thereof (—$CONH_2$→COOH).

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, d-lactate or 1-lysine, or racemic, for example, dl-tartrate or dl-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate or racemic mixture (or a racemic precursor) may be reacted with a suitable optically active compound, for example, an alcohol, or, in the case where the compound of Formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art; see, e.g., *Stereochemistry of Organic Compounds* by E. L. Eliel and S. H. Wilen (Wiley, 1994).

The present invention includes all pharmaceutically acceptable isotopically-labeled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$; carbon, such as $^{11}C$, $^{13}C$, and $^{14}C$; chlorine, such as $^{36}Cl$; fluorine, such as $^{18}F$; iodine, such as $^{123}I$ and $^{125}I$; nitrogen, such as $^{13}N$ and $^{15}N$; oxygen, such as $^{15}O$, $^{17}O$, and $^{18}O$; phosphorus, such as $^{32}P$; and sulphur, such as $^{35}S$.

Certain isotopically-labeled compounds of Formula I, for example, those incorporating a radioactive isotope, are useful in drug and/or substrate tissue distribution studies. The radioactive isotopes tritium ($^3H$) and carbon-14 ($^{14}C$) are particularly useful for this purpose in view of their ease of incorporation and ready means of detection.

Substitution with heavier isotopes such as deuterium ($^2H$) may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$, and $^{13}N$, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

When preparing compounds of Formula I in accordance with the invention, it is open to a person skilled in the art to routinely select the form of compound of Formula II which provides the best combination of features for this purpose. Such features include the melting point, solubility, processability and yield of the intermediate form and the resulting ease with which the product may be purified on isolation.

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

The compounds of the present invention dampen neuronal excitability and therefore are of value in the treatment of a wide variety of clinical diseases, disorders, or conditions that are characterized by the dysregulation of neuronal excitability in mammalian subjects, especially humans. Such diseases, disorders, or conditions include the various types of epilepsy, pain disorders, (e.g. diabetic neuropathy, fibromyalgia, migraine, post-herpetic neuralgia) and bipolar disorder (e.g., bipolar types I & II and rapid cycling). Compounds of the present invention are useful in the treatment of, for example, anxiety disorders including generalized anxiety disorder, panic disorder, PTSD, and social anxiety disorder; mood adjustment disorders including depressed mood, mixed anxiety and depressed mood, disturbance of conduct, and mixed disturbance of conduct and depressed mood; attention adjustment disorders including ADHD, attention deficit disorders or other cognitive disorders due to general medical conditions; psychotic disorders including schizoaffective disorders and schizophrenia; and sleep disorders including narcolepsy and enuresis.

Examples of the diseases, disorders or conditions which may be treated by the compound, composition and method of this invention are also as follows: depression, including depression in cancer patients, depression in Parkinson's patients, post-myocardial Infarction depression, depression in patients with human immunodeficiency virus (HIV), Sub-syndromal Symptomatic depression, depression in infertile women, pediatric depression, major depression, single episode depression, recurrent depression, child abuse induced depression, post partum depression, DSM-IV major depression, treatment-refractory major depression, severe depression, psychotic depression, post-stroke depression, neuropathic pain, manic depressive illness, including manic depressive illness with mixed episodes and manic depressive illness with depressive episodes, seasonal affective disorder, bipolar depression BP I, bipolar depression BP II, or major depression with dysthymia; dysthymia; phobias, including agoraphobia, social phobia or simple phobias; eating disorders, including anorexia nervosa or bulimia nervosa; chemical dependencies, including addictions to alcohol, cocaine, amphetamine and other psychostimulants, morphine, heroin and other opioid agonists, Phenobarbital and other barbiturates, nicotine, diazepam, benzodiazepines and other psychoactive substances; Parkinson's diseases, including dementia in Parkinson's disease, neuroleptic-induced parkinsonism or tardive dyskinesias; headache, including headache associated with vascular disorders; withdrawal syndrome; age-associated learning and mental disorders; apathy; bipolar disorder; chronic fatigue syndrome; chronic or acute stress; conduct disorder; cyclothymic disorder; somatoform disorders such as somatization disorder, conversion disorder, pain disorder, hypochondriasis, body dysmorphic disorder, undifferentiated disorder, and somatoform NOS; incontinence; inhalation disorders; intoxication disorders; mania; oppositional defiant disorder; peripheral neuropathy; post-traumatic stress disorder; late luteal phase dysphoric disorder; specific developmental disorders; SSRI "poop out" syndrome, or a patient's failure to maintain a satisfactory response to SSRI therapy after an initial period of satisfactory response; and tic disorders including Tourette's disease.

Compounds of the present invention are also useful for the treatment of epilepsy, pain, and cognitive function. See, e.g., Cooper E C, Jan L Y. *Arch Neurol.* 2003 April, 60(4):496-500. Furthermore, the compounds of the present invention are useful for the treatment of central nervous system disorders, including bipolar disorder, depressive disorders, anxiety disorders, cognitive disorders, pain disorders, urogentital disorder, and epilepsy.

Compounds of Formula I and pharmaceutically acceptable salts thereof, in combination with other active pharmaceutical active ingredients are useful to treat various diseases or disorders. For example, compounds of Formula I and pharmaceutically acceptable salts thereof may be combined with anti-convulsants (e.g., acetazolamide, carbamazepine, clobazam, clonazepam, diazepam, divalproex sodium, ethosuximide, ethotoin, felbamate, fosphenytoin, gabapentin, lamotrigine, levetiracetam, mephenytoin, metharbital, methsuximide, methazolamide, oxcarbazepine, phenobarbital, phenytoin, phensuximide, pregabalin, primidone, sodium valproate, stiripentol, tiagabine, topiramate, trimethadione, valproic acid, vigabatrin, zonisamide) to treat disorders the treatment of which is facilitated by decreased neurotransmission such as epilepsy (generalized or partial seizure disorder), nonepileptic seizures such as febrile seizures, symptomatic seizures and psychogenic seizures. Because the anti-convulsants and the compounds of Formula I have differing mechanisms, the compounds of Formula I serve additional control of dysregulated excitability that the current therapies do not provide. This would be the case especially with older antiepileptics such as phenytoin and carbemazepine. See Azar N J, Abou-Khalil B W. *Semin Neurol.*, 2008 July; 28(3):305-16.

Compounds of Formula I and pharmaceutically acceptable salts thereof, in combination with mood stabilizing compounds (e.g lithium carbonate, valproic acid, lamotrigine, carbamazepine oxcarbazepine and aytipical antipsychotics [e.g., clozapine, quetiapine, olanzapine, ziprasidone]) are useful psychotherapeutics and may be used in the treatment of bipolar disorders (depressive episode, manic episode, hypomanic episode, mixed affective episode) for the treatment of mood states which is facilitated by suppressing neurotransmission. The compounds of Formula I may advantageously be used in conjunction with one or more other therapeutic agents, for instance, different antidepressant agents such as tricyclic antidepressants (e.g., amitriptyline, dothiepin, doxepin, trimipramine, butripyline, clomipramine, desipramine, imipramine, iprindole, lofepramine, nortriptyline or protriptyline), monoamine oxidase inhibitors (e.g. isocarboxazid, phenelzine or tranylcyclopramine) or 5-HT re-uptake inhibitors (e.g., fluvoxamine, sertraline, fluoxetine or paroxetine), and/or with antiparkinsonian agents such as dopaminergic antiparkinsonian agents (e.g., levodopa, preferably in combination with a peripheral decarboxylase inhibitor e.g., benserazide or carbidopa, or with a dopamine agonist e.g., bromocriptine, lysuride or pergolide). It is to be understood that the present invention covers the use of a compound of Formula (I) or a physiologically acceptable salt thereof in combination with one or more other therapeutic agents.

Compounds of Formula I and pharmaceutically acceptable salts thereof, may also be combined with a 5-HT re-uptake inhibitor (e.g., fluvoxamine, sertraline, fluoxetine or paroxetine) or a pharmaceutically acceptable salt or polymorph thereof to treat disorders the treatment of which is facilitated by modulating serotonergic neurotransmission. Such treatment concerns diseases or disorders that include hypertension, depression, chemical dependencies, anxiety disorders (including panic disorder, generalized anxiety disorder, agoraphobia, simple phobias, and social phobia), post-traumatic stress disorder, obsessive-compulsive disorder, avoidant personality disorder and sexual dysfunction (including premature ejaculation), eating disorders, obesity, cluster headache, migraine, pain, Alzheimer's disease, obsessive-compulsive disorder, panic disorder, memory disorders (including dementia, amnestic disorders, and age-associated memory impairment), Parkinson's diseases (including dementia in Parkinson's disease, neuroleptic-induced Parkinsonism and tardive dyskinesias), endocrine disorders (including hyperprolactinaemia), vasospasm (particularly in the cerebral vasculature), cerebellar ataxia, gastrointestinal tract disorders (involving changes in motility and secretion) chronic paroxysmal hemicrania and headache (associated with vascular disorders).

The compounds of this invention can be administered via either the oral, parenteral (such as subcutaneous, intravenous, intramuscular, intrasternal and infusion techniques), rectal, intranasal or topical routes to mammals. In general, these compounds are most desirably administered to humans in doses ranging from about 1 mg to about 2000 mg per day, although variations will necessarily occur depending upon the weight and condition of the subject being treated and the particular route of administration chosen. However, a dosage level that is in the range of from about 0.1 mg to about 20 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

Pharmaceutically acceptable salts of the compounds of Formula I include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandelates mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, salicylate, saccharate, stearate, succinate, sulfonate, stannate, tartrate, tosylate, trifluoroacetate and xinofoate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002).

Pharmaceutically acceptable salts of compounds of Formula I may be prepared by one or more of three methods:
  (i) by reacting the compound of Formula I with the desired acid or base;
  (ii) by removing an acid- or base-labile protecting group from a suitable precursor of the compound of Formula I or by ring-opening a suitable cyclic precursor, for example, a lactone or lactam, using the desired acid or base; or
  (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

Biological Assay for Kv7.2/3 Channel Opening Activity

Plasmid Constructs:

Human Kv7.2 and Kv7.3 clones were obtained from GeneDynamics (Eugene, Oreg.). Both human Kv7.2/pIRESneo3 and human Kv7.3/pIREShygro3 expression vectors were constructed using a combination of fragments amplified from a human hippocampus library (extending from a NheI site near the 5' end through the stop codon) and synthetic oligonucleotides (extending from the start codon to the BamHI site). The entire construct for Kv7.2 and Kv7.3 was subcloned into the pIRESneo3 and pIREShygro3 expression vectors (Clonetech, Mountain View, Calif.), respectively, using NheI/BamHI sites introduced on either side of the start and stop codons. The construct was sequenced in its entirety to make sure that no mutations were introduced during the amplification and cloning process. Adapted from Wickendon, A D et al., *Mol Pharmacol* 58(3):591-600, 2000.

Construction of CHO-K1 Cell Line Expressing Human Kv7.2 and Kv7.3 Voltage-Gated Potassium Channel Subunits Transfection Vectors Human Kv7.2/pIRESneo3 plasmid DNA (containing the Kv7.2 gene, accession #NM_172107).

Human Kv7.3/pIREShyg3 plasmid DNA (containing the Kv7.3 gene, accession #NM_004519).

Cell Line Construction:

Chinese hamster ovary (CHO-K1) cells were transfected with human-Kv7.2 in a pIRESneo3 plasmid DNA vector (Clonetech, Mountain View, Calif.) and the h-Kv7.3 subunit in pIREShygro3 plasmid DNA vector using Lipofectamine2000™ reagent (InVitrogen, San Diego, Calif.), according to the manufacturers instructions. Cells stably expressing the human Kv7.2 and Kv7.3 constructs were identified by their resistance to 400 mg/ml, geneticin (Gibco #10131-027) and 400 mg/ml, hygromycin-B (Invitrogen #10687-010). Clones were screened for functional expression using the whole-cell, voltage-clamp technique.

Biological Assay

To determine if compounds can enhance voltage-dependent K-current in Kv7.2/7.3 channel containing CHO-K1 cells. Planar patch-clamp is used on IonWorks to functionally determine percent enhancement of Kv7.2/7.3-current at 0 mV (compared to retigabine) and potency ($EC_{50}$) of compounds. Intrinsic activity and/or potency may be important in determining in vivo pharmacological efficacy of the compounds.

Compound Preparation:

Serial dilutions were made in DMSO on an Apricot Personal Pipettor. Compounds were then diluted in external buffer on a 384 well assay plate (final DMSO concentration=0.3%).

Method:

Cells used in this assay were CHO-K1 expressing Kv7.2/7.3 channels. Cells were maintained in growth media containing: F-12 (Gibco #11765-054), 10% FBS (Invitrogen 16140-071), 1:100 Glutamax (Gibco #35050-061), 1:100 Penicillin/streptomycin (Gibco #15140-122), 400 mg/ml Geneticin (Gibco #10131-027), 400 mg/ml Hygromycin-B (Invitrogen #10687-010). Cells were grown in T-150 flasks to a confluence of approx. 80%. External recording buffer contained (in mM): NaCl (137), KCl (4), $MgCl_2$ (1), $CaCl_2$ (1.8), HEPES (10), and glucose (10), pH was adjusted to 7.3 with NaOH and osmolarity was adjusted to 300-305 mOsM with sucrose, if necessary. Internal buffer contained (in mM): Kgluconate (120), KCl (20), NaCl (5), $MgCl_2$ (1), $CaCl_2$ (2), HEPES (10), KF (2), and Na2ATP (2). Na2ATP was added to internal buffer right before use and pH was adjusted to 7.2 with KOH. Osmolarity of internal buffer was adjusted to 290-295 mOsM.

Cells were washed 1× with Ca/Mg free PBS and then removed from the plates with a 50:50 mixture of versene (Gibco 15040): 0.25% trypsin-EDTA (Gibco 25200) (4 min), trituated, centrifuged at ~1000 rpm for 5 min, and resuspended at ~2.5 million cells/ml in external buffer for recording on IonWorks. Potassium current measurements were made using an IonWorks Quattro instrument (MDS Corp.) using PatchPlate PPC substrates with 64 apertures per well. IonWorks calculated leak current was digitally subtracted from the total current acquired. Potassium current was elicited by stepping from −80 mV to 0 mV (2 sec) was measured in the absence and presence of increasing concentrations (½ log) of unknown compound (7-point concentration curves). Retigabine was run as a positive control and comparator on each PatchPlate PPC. Maximum increase in K current was determined by subtracting the current elicited in external buffer alone wells from the current elicited in wells with compound treatment (both at 0 mV). A sample size of 8 wells per treatment condition was used. Six compounds could be run on each PatchPlate. Compound dilutions were made in 384 well assay plates using an Apricot Personal Pipettor (Apricot Designs, Inc.). Pre-scan vs post-scan current run-down (~5-20%) in control wells was calculated and subtracted from the compound treated wells. Wells with pre-scan seal resistances of <40 Mohm or currents of <50 pA were excluded from the analysis.

Maximum potassium current enhancement, as a % of max retigabine enhancement, was reported as well as $EC_{50}$ values for each compound. $EC_{50}$ values in nM units. Compounds of the invention analyzed by this assay have been found to have significant activity in opening Kv7.2/3 channels with $EC_{50}$ values <100 uM.

Safety Studies—Behavioral Observations

It was recognized that rats treated with certain compounds would exhibit serious adverse events, e.g., convulsions, morbid sedation, etc. Efforts were undertaken to find compounds that did not cause convulsions with sufficient safety margins relative to an efficacious dose. Each compound tested was tested in four animals at three doses, with the lowest dose being 1 mg/kg and the highest dose tested being 100 mg/kg.

All experiments complied with laboratory guidelines, e.g., National Research Council Publication, "Guide for the Care and use of Laboratory Animals." Male Wistar Han IGS (CRL: WI [Han]) rats from Charles River Laboratories were used; they 8-9 weeks of age at dose initiation (200-250 g). Each compound was diluted in vehicle that was an aqueous solution of 0.5% (w/v) methylcellulose. The test compound was diluted in the vehicle and kept continuously stirred until administration. All dose levels are expressed as mg of active drug moiety per kg of body weight per day. Doses were administered by oral gavage once daily for 1 day. The dose volume for all animals was 10 mL/kg based on the most recent individual body weight.

On dosing days, clinical signs of treated animals were recorded predose and approximately 0.5, 1-2, and 4 hours postdose (HPD), at the end of the day, and at 24 HPD. All scheduled clinical observations were performed after the last animal dosed. See, e.g., Henshall, David C, et al, Neuropsychiatric Disease Treatment 2009:5 189-206.

Blood was collected for determination of compound concentrations at 1, 3, 7, and 24 HPD using standard procedures. Samples were stored at −20° C. or lower prior to analysis. In determining the lowest dose causing an adverse event, only one of four animals would have to have an adverse event for that dose to be identified. Table 1 Summarizes and compares the behavioral observations seen doses and exposures seen in internal studies. Example 1 shows a clear improvement over Kv7 opener standard retigabine, 69× verses 3.9× respectively with regards to serious adverse events.

TABLE 1

Comparision of side effect profile and in vivo exposures

| Compound | Predicted human Ceff Cp, u (nM) | Rat DRF | NOEL | Threshold for MCS | Threshold for SAE |
|---|---|---|---|---|---|
| Example 1 | 13 | Dose (mg/kg) | 3 | 10 | 100 |
| | | Cmax (nM) | 54 | 99 | 866 |
| | | TI | 4.2 | 7.6 | 67 |
| Retigabine | 607 | Dose (mg/kg) | 30 | 30-50 | 50 |
| | | Cmax (nM) | 870 | 870-2386 | 2386 |
| | | TI | 1.4 | 1.4-3.9 | 3.9 |

NOEL = no observable effect limit
MCS means manageable clinical signs, e.g., onset of behaviors such as ataxia, sedation, hyperactivation sensitivity or touch, head shakes, tremors but resolve in 2-4 hours.
SAE means serious adverse event, e.g., treatment results in death, is life-threatening, requires prolongation veterinary care or results in persistent or significant disability/incapacity.
TI means toxicity index that is determined from the ratio of free brain exposure at the doses tested divided by the projected human concentration.

General Synthetic Schemes and Working Examples

The compounds of Formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the Compendium of Organic Synthetic Methods, Vol. I-XII (published by Wiley-Interscience)). Preferred methods include, but are not limited to those described below. The following schemes and examples are exemplary of the processes for making compounds of Formula I. It is to be understood, however, that the invention, as fully described herein and as recited in the claims, is not intended to be limited by the details of the following examples.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

The compounds of Formula I can be prepared by several methods known to those skilled in the art. One such method is depicted in Scheme 1 starting with substituted 2-chloropyrimidines of Formula II, which may be obtained from commercial sources or by methods known to those skilled in the art. Pyrimidines of Formula II may be nitrated by several methods known to those skilled in the art, specifically with triflic anhydride and tetramethylammonium nitrate in solvents such as methylene chloride and at temperatures ranging from −78° C. to ambient temperature to yield compounds of Formula III. Subsequently compounds of Formula III may be converted to compounds of Formula V by treatment with piperidines of Formula IV in the presence of an amine base such as triethylamine or diisopropylethylamine in solvents such as DMF or THF and at temperatures ranging from ambient temperatures to 45° C. Compounds of Formula V may be reduced to compounds of Formula VI using a variety of hydrogenation methods known to one skilled in the art, such as in the presence of a hydrogen source such as hydrogen gas or ammonium formate and in the presence of a catalyst such a palladium on carbon in solvents such as methanol or ethanol and at temperatures ranging from ambient temperatures to 45° C. and pressures ranging from atmospheric to 40 psi. The resulting primary amines of Formula VI may be acylated using a variety of methods known to one skilled in the art. Compounds of Formula I may be accessed by treating compounds of Formula VI with an acid chloride in the presence of a base such as triethylamine or potassium phosphate in a solvent such as THF and with or without dimethylaminopyridine at temperatures ranging from ambient to 80° C. Alternatively compounds of Formula I may also be access via amide coupling conditions known to one skilled in the art by treatment of compounds of Formula VI with carboxylic acids and amide coupling reagent.

pressures ranging from atmospheric to 20 psi. Subsequently compounds of Formula VII may be nitrated with a combination of triflic anhydride and tetramethylammonium nitrate in solvents such as methylene chloride and at temperatures ranging from −78° C. to ambient temperature to yield compounds of Formula V, which may be converted to compounds of Formula I by methods already described.

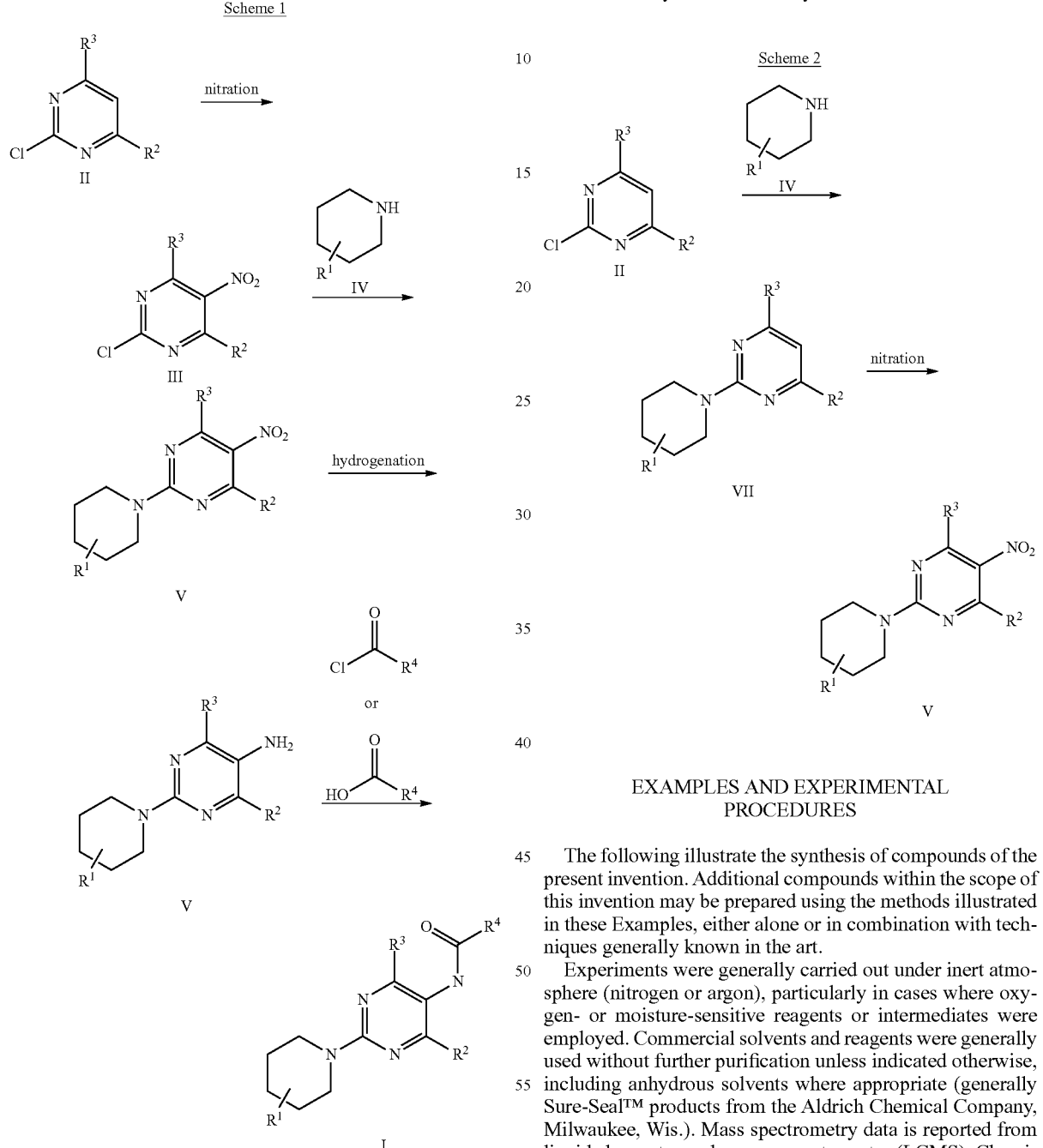

Alternatively, compounds of Formula V may be also be prepared by those skilled in the art using the method highlighted in Scheme 2 where compounds of Formula II undergo an amine coupling reaction followed by nitration. As such, substituted 2-chloropyrimidines of Formula II may be converted to compounds of Formula VII by treatment with piperidines of Formula IV in solvents such as THF and at temperatures ranging from ambient temperature to 80° C. and at

EXAMPLES AND EXPERIMENTAL PROCEDURES

The following illustrate the synthesis of compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification unless indicated otherwise, including anhydrous solvents where appropriate (generally Sure-Seal™ products from the Aldrich Chemical Company, Milwaukee, Wis.). Mass spectrometry data is reported from liquid chromatography-mass spectrometry (LCMS). Chemical shifts for nuclear magnetic resonance (NMR) data are expressed in parts per million (ppm, δ) referenced to residual peaks from the deuterated solvents employed.

For syntheses of other compounds of Formula I not specifically exemplified, reaction conditions (length of reaction and temperature) may vary. In general, reactions were followed by thin layer chromatography or mass spectrometry, and subjected to work-up when appropriate such that reaction times are approximate. Purifications may vary between

Example 1

N-(4,6-dimethoxy-2-(4-methoxypiperidin-1-yl)pyrimidin-5-yl)-3,3-dimethylbutanamide

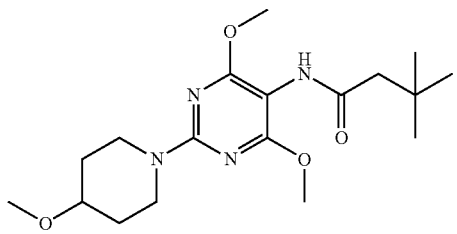 [SMILES: COc1nc(N2CCC(OC)CC2)nc(OC)c1NC(=O)CC(C)(C)C]

Step A. 2-chloro-4,6-dimethoxy-5-nitropyrimidine 2-chloro-4,6-dimethoxy-5-nitropyrimidine is known in the literature (S. A. Shackelford et al. *JOC*, 2003, 68, 267-275) and was prepared according to procedures found therein. $^1$H NMR (400 MHz, CDCl$_3$) δ 4.11 (s, 6H). LCMS m/z 219.9 (M+1) consistent with reported values.

Step B: 4,6-dimethoxy-2-(4-methoxypiperidin-1-yl)-5-nitropyrimidine

4-Methoxypiperidine (1.31 g, 11 mmol, 1 equiv) was added via syringe to a mixture of 2-chloro-4,6-dimethoxy-5-nitropyrimidine (2.5 g, 11 mmol) and diisopropylethylamine (5.97 mL, 34 mmol, 3 equiv) in THF (60 mL). The reaction mixture was stirred at RT for 1 h, and then additional 4-methoxypiperidine (0.6 g, 5 mmol, 0.47 equiv) was added via syringe. The mixture was stirred for another 1 h and then diluted with water and extracted with ethyl acetate (2×). The organic extracts were dried over sodium sulfate, filtered and concentrated. The crude material was purified using a Biotage Isolera One (SiO$_2$, 80 g, 0-80% EtOAc in heptane gradient) to afford 2.99 g (88%) of 4,6-dimethoxy-2-(4-methoxypiperidin-1-yl)-5-nitropyrimidine as a yellow solid. $^1$H NMR (400 MHz, CDCl$_3$) δ 4.14 (ddd, J=13.2, 7.5, 3.9 Hz, 2H) 3.99 (s, 6H) 3.63 (ddd, J=13.2, 8.5, 3.8 Hz, 2H) 3.51 (tt, J=7.4, 3.6 Hz, 1H) 3.40 (s, 3H) 1.86-1.96 (m, 2H) 1.61-1.70 (m, 2H). LCMS m/z=299.1 (M+1).

Step C: 4,6-dimethoxy-2-(4-methoxypiperidin-1-yl)pyrimidin-5-amine

To a 1 L Atlantis reactor, under nitrogen, was added 20% palladium on carbon (6.16 g, 5.79 mmol, 15% by weight), 4,6-dimethoxy-2-(4-methoxypiperidin-1-yl)-5-nitropyrimidine (41.1 g, 137.8 mmol) and methanol (390 mL). The reactor was sealed and purged with nitrogen (3×) and then hydrogen (3×). The mixture was hydrogenated at 50 psi (H$_2$) for 3 h. After purging with nitrogen, the catalyst was removed by filtration, and the filter cake was rinsed with additional methanol (150 mL). The filtrate was concentrated to afford 40.25 g of 4,6-dimethoxy-2-(4-methoxypiperidin-1-yl)pyrimidin-5-amine as a viscous orange oil that was used without further purification. $^1$H NMR (400 MHz, CDCl$_3$) δ 4.17-4.29 (m, 2H) 3.92 (s, 6H) 3.39 (s, 3H) 3.34-3.47 (m, 1H) 3.19 (ddd, J=13.0, 9.0, 3.0 Hz, 2H) 2.76 (br. s., 2H) 1.87-2.00 (m, 1H) 1.43-1.68 (m, 2H). LCMS m/z=269.1 (M+1).

Step D: Example 1

To a solution of 4,6-dimethoxy-2-(4-methoxypiperidin-1-yl)pyrimidin-5-amine (36.97 g, 137.8 mmol), triethylamine (15.25 g, 21.0 mL, 150.7 mmol) in ethyl acetate (370 mL) was added tert-butylacetyl chloride (20.26 g, 21.0 mL, 150.5 mmol, 1.1 equiv) dropwise over 15 min. The resulting suspension was stirred overnight at RT, then poured into water, stirred 30 min, and subsequently transferred to a separatory funnel rinsing with ethyl acetate (100 mL). The organic extract was separated and washed with brine (100 mL), dried over magnesium sulfate, filtered, and concentrated to provide yellow-orange solids, which were taken up in 1:1 heptane:methyl tert-butylether (500 mL) and stirred at RT. The resulting suspension was filtered, and the solids were washed with 1:1 heptane: methyl tert-butylether (100 mL) and dried to afford 39.76 g of N-(4,6-dimethoxy-2-(4-methoxypiperidin-1-yl)pyrimidin-5-yl)-3,3-dimethylbutanamide, Example 1, as a white solid. $^1$H NMR (CDCl$_3$) δ 6.14 (br. s., 1H) 4.23 (ddd, J=14.2, 5.7, 4.5 Hz, 2H) 3.87 (s, 6H) 3.40-3.48 (m, 1H) 3.39 (s, 3H) 3.37 (assumed ddd, J=13.5, 9.2, 3.3 Hz, 2H partially obscured by singlet) 2.20 (s, 2H) 1.83-1.99 (m, 2H) 1.47-1.61 (m, 2H) 1.10 (s, 9H). MS: (ESI) m/z=367.2 (M+1).

The invention claimed is:
1. The compound N-(4,6-dimethoxy-2-(4-methoxypiperidin-1-yl)pyrimidin-5-yl)-3,3-dimethylbutanamide, or a pharmaceutically acceptable salt thereof.
2. The compound N-(4,6-dimethoxy-2-(4-methoxypiperidin-1-yl)pyrimidin-5-yl)-3,3-dimethylbutanamide.
3. A pharmaceutically acceptable salt of the compound N-(4,6-dimethoxy-2-(4-methoxypiperidin-1-yl)pyrimidin-5-yl)-3,3-dimethylbutanamide.
4. A pharmaceutical composition, comprising the compound N-(4,6-dimethoxy-2-(4-methoxypiperidin-1-yl)pyrimidin-5-yl)-3,3-dimethylbutanamide, or a pharmaceutically acceptable salt thereof and at least one additional pharmaceutically acceptable excipient.

* * * * *